(12) United States Patent
Berlin et al.

(10) Patent No.: US 8,058,041 B2
(45) Date of Patent: Nov. 15, 2011

(54) CONCURRENT SACCHARIFICATION AND FERMENTATION OF FIBROUS BIOMASS

(76) Inventors: Alex Berlin, Vancouver (CA); Edward Kendall Pye, Vancouver (CA); Donald O'Connor, Delta (CA)

( * ) Notice: Subject to any disclaimer, the term of this patent is extended or adjusted under 35 U.S.C. 154(b) by 762 days.

(21) Appl. No.: 12/167,880

(22) Filed: Jul. 3, 2008

(65) Prior Publication Data

US 2009/0011484 A1    Jan. 8, 2009

Related U.S. Application Data

(60) Provisional application No. 60/947,962, filed on Jul. 4, 2007.

(51) Int. Cl.
*C12P 7/10* (2006.01)

(52) U.S. Cl. ..................... 435/165; 435/289.1

(58) Field of Classification Search .................. 435/165, 435/289.1
See application file for complete search history.

(56) References Cited

U.S. PATENT DOCUMENTS 7,413,882 B2 *   8/2008   Berka et al. .................. 435/105

OTHER PUBLICATIONS

Keating et al "Tolerance and Adaptation of Ethanologenic Yeast to Lignocellulosic Inhibitory Compounds" J. Biiotecknology Bioeng Apr. 20, 2006 vol. 93 No. 6 1196-1206.*

* cited by examiner

*Primary Examiner* — Herbert J Lilling
(74) *Attorney, Agent, or Firm* — Gowling Lafleur Henderson

(57) ABSTRACT

A process for simultaneous saccharification and fermentation of a cellulosic solids fraction extracted from a lignocellulosic feedstock. The viscosity of the cellulosic solids fraction is reduced by intermixing with a liquid carbohydrate stream. A suitable liquid carbohydrate stream is a de-lignified liquids fraction that was previously separated from the solids fraction during processing of the lignocellulosic feedstock. Alternatively, the viscosity of the solids fraction may be reduced by commingling with a liquid carbohydrate stream comprising one or more monosaccharides. The reduced-viscosity cellulosic solids fraction is then commingled with a fermentative microbial inoculant and a cellulosic biomass-degrading enzyme composition. The commingled mixture is maintained in a pressurized reaction vessel under elevated temperatures to enable simultaneous enzymatic hydrolysis of the cellulosic solids to monosaccharides and fermentation of the monosaccharides to produce an ethanolic beer. The ethanolic beer is distillable for recovery of fuel-grade ethanol and a stillage that may be further processed.

28 Claims, 5 Drawing Sheets

CONCURRENT SACCHARIFICATION AND FERMENTATION OF FIBROUS BIOMASS

RELATED APPLICATION

This application claims the benefit of U.S. provisional patent application No. 60/947,962 filed Jul. 4, 2007, which is hereby incorporated by reference.

TECHNICAL FIELD

This invention relates to systems and methods for fractionation of fibrous biomass into component parts. More particularly, this invention relates to the concurrent production and fermentation in a single vessel, of carbohydrates from lignocellulosic materials.

BACKGROUND OF THE INVENTION

Naturally occurring fibrous biomass produced by plants typically contains a variety of hexose carbohydrates such as glucose, galactose and mannose that are readily fermentable by ethanologenic yeasts to ethanol. Glucose is the sole component of cellulose, but it is also a significant component of hemicellulose, especially in softwoods. Galactose and mannose are the other major hexose carbohydrates that exist in hemicellulose. When *Saccharomyces* spp. yeasts, typically used in the industrial production of ethanol, are presented with feedstocks comprising mixtures of glucose, galactose and mannose, they will first ferment the glucose and after it is exhausted from the medium, the yeast cells will then adapt to taking up and fermenting the mannose, and then after the mannose is depleted, the yeast will adapt again for metabolizing galactose, which is the most difficult to ferment of the three main carbohydrates derived from hemicelluloses. This type of adaptive metabolic behaviour is called diauxic growth or metabolism (for two carbohydrates) and triauxic growth or metabolism (for three carbohydrates). Between each phase of carbohydrate utilization, there is normally a period of several hours during which time no fermentation occurs while the required transport proteins are induced in the cell membrane of the yeast. This induction phenomenon typically results in significantly extended fermentation times required for complete consumption of mixtures of fermentable carbohydrates derived from hemicellulose. In industrial processes configured for production of ethanol from mixed hexose-carbohydrate feedstock streams produced from lignocellulosic materials such as angiosperm fibers, gymnosperm fibers, and field crop fibers, the fermentation delays caused by enzymatic adjustments during diauxic and triauxic metabolism significantly increase the capital and operating expenditures associated with these processes. Accordingly, strain selection strategies are commonly employed to identify and select yeast stains that are potentially suitable for industrial fermentation processes, based on their efficiencies of converting liquid hexose streams into ethanol in laboratory-scale systems. Suitable exemplary yeast strains for fermenting liquid hexose streams include *Saccharomyces cerevisiae* T1 for sequentially metabolizing glucose-mannose-galactose, and *S. cerevisiae* Y-1528 for sequentially metabolizing galactose-glucose-mannose (Keating et. al., 2004, J. Ind. Microbiol. Biotechnol. 31:235-244).

The initial stages of industrial-scale processing of lignocellulosic fibrous materials commonly include physico-chemical disruption of the fibers followed by chemical extraction of the disrupted materials using solvents, dilute acid and/or biological conversion of the disrupted materials. The solvent extraction processes typically result in separation of lignins from the oligosaccharide and polysaccharide constituents of the fibers, causing the release of lignins and at least some of the monosaccharides, oligosaccharides and polysaccharides into the extraction solvents. Following the recovery of the solvents, the spent aqueous extraction liquors may then be used as feedstock streams for ethanol production. However, the spent extraction liquors also typically contain significant amounts of lignocellulosic-derived organic compounds such as ketones, aldehydes, carboxylic acids and other such compounds that significantly impair or inhibit microbial fermentative metabolic processes. Such inhibitors are exemplified by furfural, 5-hydroxymethyl furfural, acetic acid and the like. Consequently, selection criteria for identifying commercially useful fermentative microorganisms also include assessments of their tolerance and metabolic performance during extended periods of exposure to inhibitors. Keating et al., 2006, Biotechnol. Bioeng. 93: 1196-1206 have shown that while the fermentation rates of *S. cerevisiae* strains T1 and Y-1528 declined as the levels of selected inhibitors contained in liquid hexose streams were increased, the overall yields of ethanol in laboratory-scale batch fermentations were not affected.

SUMMARY OF THE INVENTION

The exemplary embodiments of the present invention are directed to industrial-scale processes, systems and methods configured for concurrent downstream saccharification and fermentation of structural components released during upstream extraction of fibrous lignocellulosic feedstocks. Exemplary fibrous lignocellulosic structural components suitable for the industrial-scale concurrent saccharification and fermentation processes, systems and methods of the present invention provided, described and anticipated herein, comprise celluloses, hemicelluloses, polysaccharides and oligosaccharides.

According to one exemplary embodiment of the present invention, there is provided processes for concurrent saccharification and fermentation of structural components released during the organic solvent extraction of fibrous lignocellulosic feedstocks. An exemplary process generally comprises the steps of processing a selected lignocellulosic feedstock with an organic solvent to produce commingled solids fraction and liquid fraction, separating the solids fraction from the liquid fraction, intermixing the separated solids fraction with a selected liquid monosaccharide and/or oligosaccharide or mixed monosaccharide/oligosaccharide stream to reduce the viscosity of the separated solids fraction, after which, the reduced-viscosity solids fraction is commingled with an effective amount of an inoculum comprising a suitable microbial culture selected for fermentation of pentose and/or hexose carbohydrates, additionally adding thereto effective amounts of suitable enzymes for saccharification of the polysaccharides and oligosaccharides, and then providing suitable reaction conditions for a suitable period of time for saccharification of the solids fraction and fermentation of the monosaccharides and/or oligosaccharides if the microorganism has the ability to ferment oligosaccharides.

Suitable solids fractions may be produced from fibrous lignocellulosic feedstocks exemplified by angiosperm biomass, gymnosperm biomass, field crop biomass, vegetative and/or fruit pulps, wood and wood processing scraps and waste materials, recyclable paper and cardboard goods, and the like.

Suitable liquid streams for reducing the viscosity of solids fractions separated from extracted lignocellulosic feedstocks are exemplified by de-lignified liquid fractions separated from the extracted lignocellulosic feedstocks. Other suitable liquid streams are exemplified by carbohydrate-containing solutions comprising water, short-chain alcohols, acids, bases and the like. The liquid streams may be further supplemented with one or more selected monosaccharide carbohydrates such as those exemplified by glucose, galactose and mannose and the like.

Suitable microbial inocula for fermenting pentose and/or hexose carbohydrates comprise one or more suitable strains selected from yeast species, fungal species, bacterial species, protozoae, or other species. Suitable yeasts are exemplified by *Saccharomyces* spp. and *Pichia* spp. Suitable *Saccharomyces* spp are exemplified by *S. cerevisiae* such as strains Y1528, Tembec-1 and the like. Suitable fungal species are exemplified by *Aspergillus* spp. and *Trichoderma* spp. Suitable bacteria are exemplified by *Escherichia coli, Zymomonas* spp, *Clostridium* spp. and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria).

Suitable enzymes are exemplified by cellulases, hemicellulases, β-glucosidases, β-xylosidases, α-amylases, β-amylases, and other glycanases.

One aspect of the present invention is the recovery and recycling of the liquid fractions separated from solids fractions of extracted fibrous lignocellulosic feedstocks. Lignin extracted into the solvent during processing of the lignocellulosic feedstock, is separated from the liquid fractions. De-lignified liquid fractions or alternatively, partially de-lignified liquid fractions are suitable diluents for reducing the viscosity of the separated solids fractions. It is suitable to amend the de-lignified liquid fractions with one or more monosaccharide carbohydrates prior to their use for reducing the viscosity of solids fractions. Suitable monosaccharide carbohydrates are exemplified by glucose, mannose, galactose and the like.

According to one aspect, the processes are batch processes.

According to another aspect, the processes are continuous processes.

According to yet another aspect, the processes are semi-continuous processes.

According to another embodiment of the present invention, there is provided systems for concurrent saccharification and fermentation of solids fractions separated from extracted fibrous lignocellulosic feedstocks. The systems generally comprise: (a) a supply of extracted fibrous lignocellulosic feedstock separable into a solids fraction and a liquid fraction, (b) a plurality of suitable apparatus and operating systems configured for separately receiving and processing therein solids and liquid fractions separated from extracted lignocellulosic feedstocks, (c) a supply of a suitable liquid stream enriched with fermentable carbohdyrates selected for reducing the viscosity of the solids fraction, (d) a supply of a suitable microbial culture, (e) suitable selected enzymes, and (f) devices, apparatus, instruments and software for controllably commingling the solids fraction, the liquid stream, microbial culture, and enzymes, into a reaction mixture comprising reaction products exemplified by lignins and ethanol. A suitable liquid stream is exemplified by a liquid fraction recovered from the extracted fibrous lignocellulosic feedstock and then de-toxified or non-detoxified and ethanol removed fully or partially prior to commingling with the solids fraction for reducing the viscosity thereof. Ethanol separated from the reaction mixture is usable as a fuel or alternatively as a fuel component or other non-fuel related applications after further purifying it such as applications in the pharmaceutical, food and feed industries.

According to one aspect, the system may be additionally configured to receive and de-toxify therein liquid fractions enriched with fermentable carbohydrates separated from extracted lignocellulosic fibrous materials, comprising suspended particulate celluloses, hemicelluloses, polysaccharides, and oligosaccharides.

According to another aspect, the system may be configured to continually receive and process batches of solids factions separated from extracted lignocellulosic feedstocks, while concurrently discharging reaction products.

According to another aspect, the system may be configured to continually receive, reduce the viscosity of and further process batches of solids fractions separated from extracted lignocellulosic feedstocks, while concurrently discharging reaction products.

According to another aspect, the system is configured as a batch system.

According to yet another aspect, the system may be configured to recover and to recondition the spent organic or inorganic solvent, and to recycle said reconditioned organic or inorganic solvent.

According to a further aspect, the system is configured to recover and regenerate the spent organic or inorganic solvent, and to recycle the regenerated organic or inorganic solvent for use therein as a liquid stream for reducing the viscosity of a solids fraction separated from an extracted lignocellulosic feedstock, prior to concurrent saccharification and fermentation of said solids fraction.

According to yet another exemplary embodiment of the present invention there is provided a method for concurrent saccharification and fermentation of solids fractions separated from extracted fibrous lignocellulosic feedstocks, comprising commingling a separated solids fraction with a suitable organic or inorganic solvent comprising carbohydrates therein, with an effective amount of a suitable microbial culture selected for fermentation of pentose and/or hexose carbohydrates, and with an effective amount of suitable enzymes. Suitable organic or inorganic solvents comprising carbohydrates therein are exemplified by liquid fractions separated from extracted lignocellulosic feedstocks, and then de-toxified or non-detoxified prior to commingling with the solids fraction. Suitable microbial cultures for fermenting pentose and/or hexose carbohydrates comprise one or more suitable strains selected from yeast species, fungal species and bacterial species. Suitable yeasts are exemplified by *Saccharomyces* spp. and *Pichia* spp. Suitable *Saccharomyces* spp are exemplified by *S. cerevisiae* such as strains Y1528, Tembec-1 and the like. Suitable fungal species are exemplified by *Aspergillus* spp. and *Trichoderma* spp. Suitable bacteria are exemplified by *Escherichia coli, Zymomonas* spp, *Clostridium* spp. and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria). Suitable enzymes are exemplified by cellulases, hemicellulases, β-glucosidases, β-xylosidases, α-amylases, β-amylases, and other such glycanases.

According to yet another exemplary embodiment of the present invention there is provided a method for concurrent saccharification and fermentation of solids fractions separated from extracted fibrous lignocellulosic feedstocks, comprising commingling a separated solids fraction with a suitable liquid stream, with an effective amount of a culture of *Saccharomyces cerevisiae* strain Y-1528 genetically modified to ferment pentose carbohydrates and to secrete biomass-degrading enzymes.

BRIEF DESCRIPTION OF THE DRAWINGS

The present invention will be described in conjunction with reference to the following drawings, in which.

DETAILED DESCRIPTION OF THE INVENTION

Figure 1:
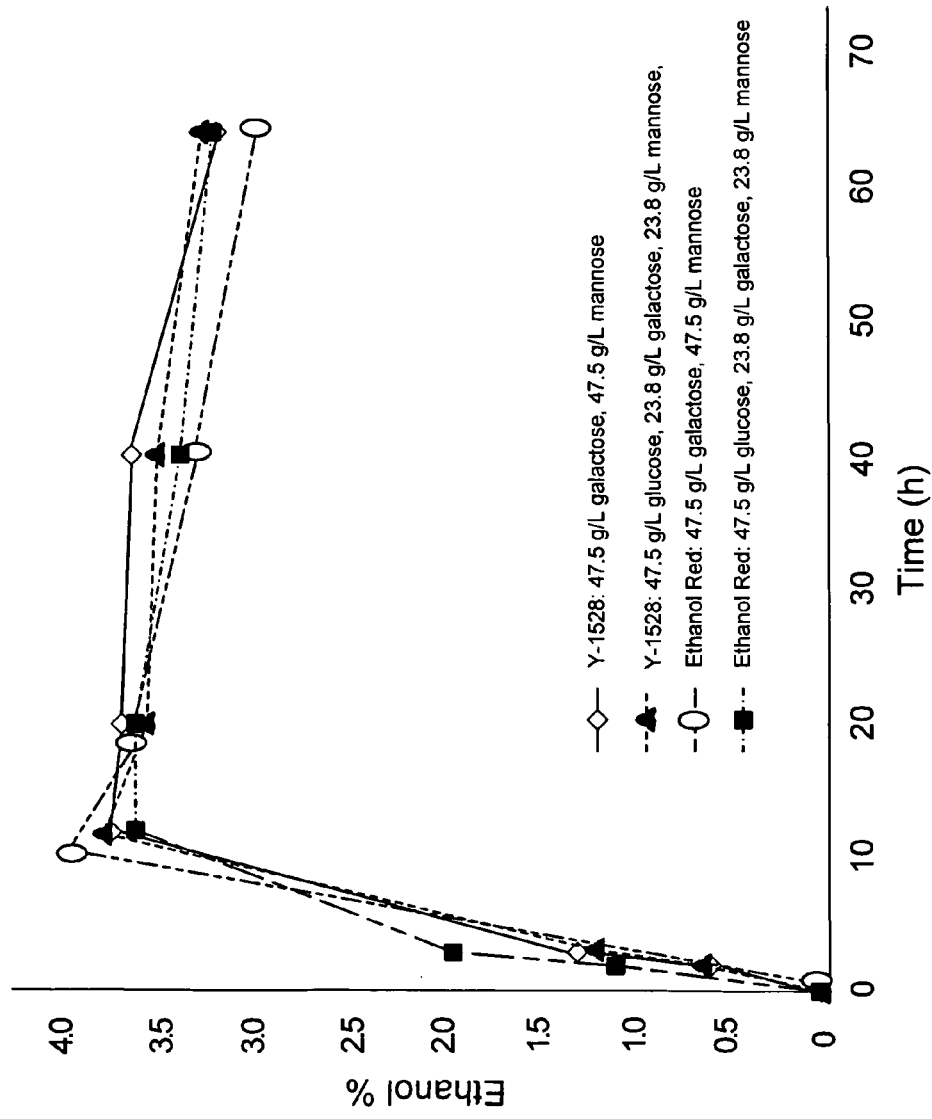
FIG. 1 is a chart comparing the fermentation efficiency of a proprietary *Saccharomyces cerevisiae* strain (Ethanol Red®; Ethanol Red is a registered trademark of Lesaffre et Compagnie, Paris, France) with a public domain *Saccharomyces cerevisiae* strain designated as "Y-1528", when cultured in solutions comprising mixtures of two or three monosaccharides. The data points are averages of triplicate samples. The bars extending above and below the data points represent±Standard Deviation (SD) at 95% confidence. Data points without SD bars encompass the SD range for those data points.

Exemplary embodiments of the present invention relate to fermentation processes and systems configured for concurrent saccharification and fermentation (CSF) of solids fractions and optionally de-toxified liquid fractions enriched with carbohydrates separated from extracted fibrous lignocellulosic materials and spent extraction solvents. Such CSF systems are also commonly referred to as simultaneous saccharification and fermentation (SSF) processes. The fermentation processes of the present invention may be configured as batch processes or alternatively, as continuous processes, or further alternatively as semi-continuous processes or fed-batch processes.

An exemplary embodiment of the present invention relates to processing a selected lignocellulosic feedstock with an organic solvent to produce a solids fraction generally comprising cellulosic fibres (i.e., a cellulose-enriched solids fraction) and a liquids fraction comprising the organic solvent into which have been solubilised various structural organic and mineral components that comprised the lignocellulosic feedstock. Suitable lignocellulosic feedstock mixtures for separation into solids and liquids fractions are exemplified by fibrous biomass from plant materials such as angiosperms, gymnosperms and field crops, vegetative and/or fruit pulps, wood and wood processing scraps and waste materials, recyclable paper, cardboard goods, and the like, and mixtures thereof. The selected lignocellulosic feedstock is commingled with a suitable solvent generally useful in organosolv processes, and then processing the lignocellulosic feedstock for a suitable period of time to enable separation of a solids component comprising cellulosic pulp and a liquids fraction comprising the organic solvent containing solubilised components such as lignins, hemicelluloses, polysaccharides, oligosaccharides among other compounds. Organosolv processes employ the use of organic chemicals such as those exemplified by short chain aliphatic alcohols (e.g., methanol, ethanol), formic acid, acetic acid, ethyl acetate, phenols & cresols, for pulping solvents that are used to solubilize and remove lignin from the fibrous plant biomass. During the solvent delignification of fibrous lignocellulosic materials, most of the hemicellulose components of the plant-based fibres are partially hydrolyzed and solubilized into the solvent. As the organosolv process proceeds toward completion, simple carbohydrates and oligosaccharides are released to the black liquor (black liquor is the combination of the solubilized lignins, carbohydrates, carbohydrate-degradation compounds, and other organic and inorganic compounds with water and the chemicals used for the extraction). These carbohydrates are then carried through the liquor processing steps including evaporation of the diluted liquid stream at boiling temperature, cooling the evaporated liquid, pH-adjusted to fermentable conditions and eventually exit the processing system as an evaporator concentrate ready to be mixed with the solids in an SSF process scheme or to be fermented separately into ethanol.

Another exemplary embodiment of the present invention relates to further processing of the evaporator concentrate for removal of lignin components or lignin-degradation, carbohydrate-degradation, extractives-degradation products thereby producing a de-toxified carbohydrate-rich organic solvent that is suitable for diluting the viscosity of the cellulose-enriched solids fraction to reduce its viscosity before commencing the simultaneous saccharification and fermentation step.

Another exemplary embodiment of the present invention relates to commingling the reduced viscosity cellulose-enriched solids fraction containing de-toxified carbohydrate-rich organic solvent, with selected microbial inocula and enzymes for enhancing the rates and efficiencies of: (a) saccharification of the cellulose-enriched solids to primarily glucose, mannose, galactose and to a lesser extent xylose, and (b) concurrent fermentation of these monosaccharides as they are produced by enzymatic hydrolysis. Suitable microbial inocula for fermenting pentose and/or hexose carbohydrates comprise one or more suitable strains selected from yeast species, fungal species and bacterial species. Suitable yeasts are exemplified by *Saccharomyces* spp. and *Pichia* spp. Suitable *Saccharomyces* are exemplified by *S. cerevisiae* and the like. Suitable fungal species are exemplified by *Aspergillus* spp. and *Trichoderma* spp. Suitable bacteria are exemplified by *Escherichia coli*, *Zymomonas* spp, *Clostridium* spp. and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria). Suitable *Saccharomyces* spp. cultures are exemplified by *S. cerevisiae* strains Y1528, Tembec-1, and may be naturally occurring strains and/or genetically engineered strains. All three major hexose carbohydrates, i.e., glucose, galactose and mannose found in fibrous biomass as exemplified by woody biomass will be fermented simultaneously by such *S. cerevisiae* strain Y-1528 cultures to ethanol, thus avoiding the long lag times and the associated higher operating costs that would be experienced by the commonly-used *Saccharomyces* yeast species and strains. The elimination of these auxotrophic-related lag times has the advantage of accelerating the total fermentation process thereby reducing the equipment size requirements and the related capital costs. Furthermore, biomass-degrading enzyme preparations normally employed in saccharification of cellulose usually have sufficient secondary activity to hydrolyze most of the hemicellulose polysaccharides and oligosaccharides derived from hemicellulose during the pretreatment step to their component monosaccharides. Therefore, because the oligosaccharides derived from hemicellulose may be optionally added to the saccharification stage of the processes of the present invention, no significant amounts of additional hemicellulose-degrading enzymes are required to maximize fermentation of various oligosaccharide components produced during the hydrolytic processes provided by extraction of fibrous lignocellulosic feedstocks. Depending on the cellulase enzyme source, there may be sufficient secondary activity to completely hydrolyze hemicelluloses that remain associated with the solid fibrous pulp. If not, additional xylanases, beta-xylosidases, esterases, and other hemicellulose-degrading enzymes may be optionally added to the saccharification mixture to achieve this desirable goal.

While the processes of the present invention wherein effective amounts of microbial cultures as exemplified by *S. cerevisiae* strain Y-1528, commingled with fibrous biomass solids fractions and suitable liquid streams, are particularly suitable for industrial SSF processes, they are also suitable for separated hydrolysis and fermentation (SHF) industrial processes. Furthermore, it is within the scope of this invention to pre-treat solids fractions separated from extracted lignocellulosic feedstocks to initiate fiber disruption and hydrolysis prior to delivery of the biomass to an SSF process or alternatively, to a SHF process.

In industrial processes where the objective is production of fuel ethanol, it is economically desirable that the concentration of ethanol produced in the beers resulting from organosolv extraction or other extraction methods suitable for fibrous lignocellulosic feedstocks is greater that 5.0-6.5% w/w. In order to achieve this target, it is necessary to have a lignocellulosic solids consistency of at least 16% (w/w) for a typical organosolv-pretreated biomass sample in the saccharification stage. A commingled solids fraction suspension with 16% solids is very thick, viscous and difficult to mix. This is the best-case of best pretreated organosolv substrates (other substrates such as steam-exploded wood or dilute acid-pretreated agricultural residues will require much higher consistencies (30-40%) to achieve this target due to the high content of non-fermentable components such as ash (5-15%) and lignin (20-40%). Organosolv-treated solids fractions from extracted lignocellulosic substrates do not have this problem since optimally extracted substrates have ash content less than 0.5% and lignin content less than 5%. Accordingly, another embodiment of the present invention provides processes incorporating therein strain *S. cerevisiae* Y-1528 wherein a liquid stream comprising carbohydrate mixtures is intermixed with the solid lignocellulosic material thereby providing a lower consistency, i.e., lower viscosity of solids which in turn facilitates the achievement of final ethanol concentrations in the beer that are in excess >5.0-6.5%. One aspect of incorporating an intermixing liquid carbohydrate stream is that some monosaccharides in the form of xylose, for example, will be present at early stages of hydrolysis of the fibrous lignocellulosic material. The attendant presence of xylose will provide the yeast with a carbon source necessary for its metabolism and viability, which is usually absent at the early stages of hydrolysis in most raw fibrous biomass feedstocks. The provision of a supplementary liquid carbohydrate stream according to this embodiment will facilitate more complete utilization of the mixed hexose carbohydrates that are derived from woody or non-woody biomass comprising agricultural residues, thereby resulting in less waste and lower waste treatment costs in lignocellulose biorefineries configured for processing these types of lignocellulosic feedstocks. This will also facilitate at a later stage the fermentation of pentose carbohydrates into ethanol by naturally occurring pentose-fermenting microorganisms such as *Pichia stipitis* which are generally repressed by the presence of glucose. This embodiment may also reduce the energy costs associated with the requisite mixing of highly viscous fibrous material in SHF or SSF systems, while facilitating production of final ethanol concentration in excess of 5.0-6.5% w/w in beer. Additionally, this embodiment may enable lower microbial loading, i.e. reducing the amount of yeast culture required for efficacy, since higher concentrations of hexose and pentose carbohydrates would be available for yeast metabolism and to maintain viability during the early stages of cellulose solids hydrolysis and fermentation.

According to this embodiment, a solid cellulosic fraction at high consistency (>40%) would be diluted to the consistency suitable for either SSF or SHF (~20%) with an aqueous liquid stream containing a mixture of monosaccharides and oligosaccharides derived from solvents used for extraction of lignocellulosic feedstocks. Suitable pretreatment processes are exemplified by organosolv, steam-explosion, dilute acid hydrolysis, ammonia fiber explosion (AFEX), and the like. Furthermore, it is within the scope of this invention for a suitable cellulase, hemicellulase, and other biomass-degrading enzymes blend to be premixed into the liquid carbohydrate stream, thereby further facilitating complete hydrolysis of both the oligosaccharides and the solid fibrous cellulose-rich fraction. In SSF processes, an effective amount of a suitable microbial inoculum would be added to the mix, thereby providing fermentation means concurrent with the saccharification processes. Suitable microbial inocula comprise at least one strain selected from yeast species, fungal species and bacterial species. Suitable yeasts are exemplified by *Saccharomyces* spp. and *Pichia* spp. Suitable *Saccharomyces* are exemplified by *S. cerevisiae* and the like. Suitable fungal species are exemplified by *Aspergillus* spp. and *Trichoderma* spp. Suitable bacteria are exemplified by *Escherichia coli*, *Zymomonas* spp, *Clostridium* spp. and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria).

In SHF processes, the saccharification would proceed first followed by the fermentation. Following complete fermentation, the resultant ethanol beer is distillable to recover ethanol. The remaining stillage may be further processed to recover: (a) residual lignin suitable as feedstocks or alternatively, as raw materials for producing lignin-based plastic, adhesive, antioxidant, surfactant, coating materials and the like, (b) yeast cells for conversion into feed protein or recycling to be reused in an ethanol production process, (c) xylose and/or arabinose for use as raw materials by the food industry or to be fermented by a microorganism or by the means of a chemical process into ethanol or other useful chemical such as xylitol, while (d) any remaining liquids are processable by aerobic or anaerobic waste treatment facilities.

The processes, systems and methods of the present invention for concurrent downstream saccharification and fermentation of structural components released during upstream extraction and fractionation of fibrous lignocellulosic feedstocks are described in more detail in the following examples which are intended to be exemplary of the invention and are not intended to be limiting.

EXAMPLE 1

A dry culture of the Red Ethanol® *S. cerevisiae* strain was obtained from PhibroChem (Ridgefield Park, N.J., USA). A culture of *S. cerevisiae* strain Y-1528 was obtained from the United States Agricultural Research Service Culture Collection, National Center for Agricultural Utilization Research (Peoria, Ill., USA). Yeast inocula were prepared by culturing the yeast strains on agar plates. Two-L Erlenmeyer flasks were each provided with 600 mL of growth medium containing 1% yeast extract and 1% peptone supplied by BioShop Canada Inc. (Burlington, ON, Canada) and 2% glucose (Sigma, St. Louis, Mo., USA). The pH was adjusted to 5.5 with 10% v/v HCl. The flasks were inoculated with yeast colonies picked from the agar plates after which, the inoculated media were incubated overnight at 30° C. under micro-aerobic conditions with agitation at 250 rpm.

The fermentation experiments were run in 250-mL Erlenmeyer flasks, each containing 100 mL of 0.1 M citrate buffer (pH 5.5). Two sets of flasks were prepared. The first set of flasks received: (a) 47.5 g/L mannose, and (b) 47.5 g/L galactose. The second set of flasks received: (a) 47.5 g/L mannose, (b) 47.5 g/L galactose, and (c) 47.5 g/L glucose. Each flask also received 0.5 ppm of the antibiotic Lactrol® (Lactrol is a registered trademark of the Phibro Animal Health Corp., Fort Lee, N.J., USA). The fermentation performance of each yeast strain in these media was tested in duplicate by adding 3 g/L odw of yeast cells harvested from the yeast extract-peptone growth medium to selected flasks and then incubating the inoculated flasks at 36° C. Samples of the supernatants in each flask were taken at 0, 1, 2, 3, 12, 20, 40, and 64 h and were analyzed: (a) for ethanol content by gas chromatography (GC), and (b) for carbohydrate content by HPLC.

The results of this study are shown in FIG. 1. The Red Ethanol® *S. cerevisiae* strain is a specially selected strain that was developed for the industrial ethanol industry. This strain has high tolerance to ethanol and was designed for producing alcohol at elevated temperatures. The data in FIG. 1 indicate that the fermentation performance of the public domain *S. cerevisiae* strain Y-1528 at an elevated temperature (i.e., 36° C.) was similar to the Red Ethanol® strain in both the galactose-mannose substrate and in the galactose-mannose-glucose substrate. Within 12 h after inoculation, both yeast strains reached the ethanol concentration maxima of about 4.8% w/w ethanol which corresponds to an overall ethanol theoretical yield of about 76%. None of the carbohydrates were present in detectable concentrations in the supernatants indicating that full consumption was achieved by both *S. cerevisiae* strains.

EXAMPLE 2

The ethanol production performance of the *S. cerevisiae* strain Y-1528 in a SSF system was assessed using a hardwood pulp produced from aspen wood chips (designated as Asp4). The Asp4 pulp was prepared from representative samples of British Columbian aspen (*Populus tremula*) logs, which were harvested, debarked, split, chipped and miled to a chip size of approximately 20 mm×20 mm×3 mm. The chips were stored at ambient temperatures in aerated plastic bags until their moisture content reached about 10%. Two hundred grams (o.d.w.) of air-dried chips were then organosolv-pretreated for 30 min at 195° C. in a custom-built batch high-pressure reactor (Parr Instrument Co., Moline, Ill., USA) containing an aqueous ethanol solution (50%; w/w) using 0.55% sulfuric acid as a catalus) at a liquor:wood ratio of 5:1. After the 30-min cooking period, the reactor was cooled to ambient room temperature using a water cooling coil. Solids and liquor were then separated by filtering. The solids fraction was homogenized in a British disintegrator using a warm 70% ethanol solution (v/v) and then washed with water. The washed solids fraction, i.e., pulp, was squeezed in a hydraulic press to reduce the final moisture content to about 50% (w/w). The final Asp4 pulp was chemically analyzed to determine its composition: (a) arabinan=0%, (b) galactan=0%, (c) glucan=84.87%, (d) xylan=5.71, (e) mannan=1.59, and (f) lignin=2.94%.

Figure 2:
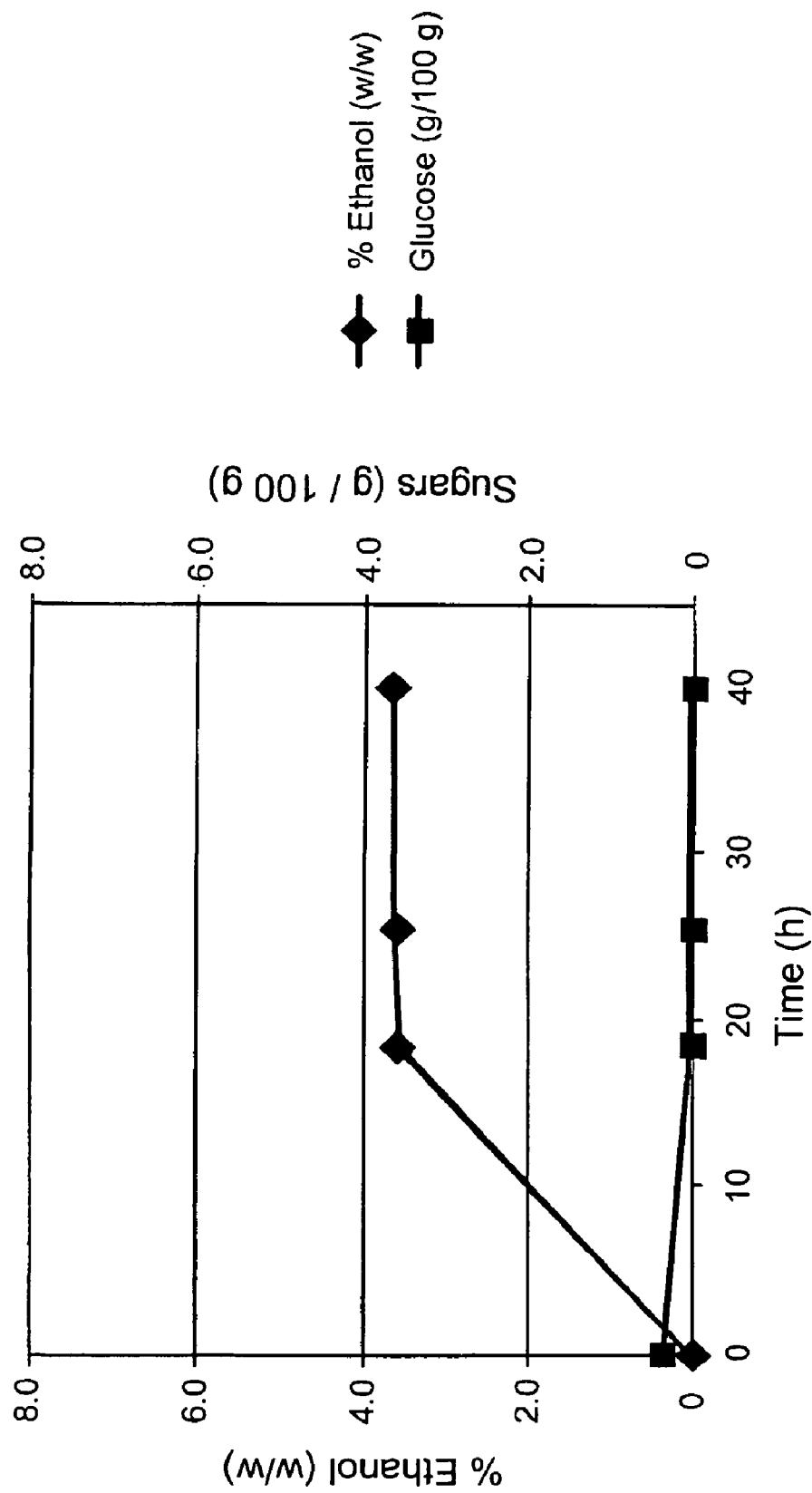
FIG. 2 is a chart showing the rate of ethanol production by *S. cerevisiae* strain Y-1528 when cultured in a simultaneous saccharification and fermentation system using a hardwood solids fraction obtained from aspen by Lignol lab-scale pretreatment technology supplemented as the fermentation substrate. The data points are averages of triplicate samples. The bars extending above and below the data points represent±Standard Deviation (SD) at 95% confidence. Data points without SD bars encompass the SD range for those data point.

The reaction mixture for this study comprised 16.0 g of Asp4 "wet" pulp diluted to 8% with 68.24 mL of 0.1 M citrate buffer in a 2.0 L Erlenmeyer flask. The solids content of the ASP4 pulp was 48.23% while the glucan content was 93%. The reaction mixture was augmented with 0.05 g/L of Lactrol®, and 2 g of a yeast nutrient mixture comprising 1.7 g/L of Yeast Nitrogen Base (Prod. No. YNB404; BioShop Canada Inc.), 2.27 g/L urea (Prod. No. URE002; BioShop Canada Inc.), and 6.56 g/L peptone (Prod. No. PEP403; BioShop Canada Inc.). A *Trichoderma reesii* cellulase enzyme preparation (Novozym 50013; Novozymes, Franklinton, N.C., USA) was added to provide 20.0 FPU/g glucan (FPU=filter paper units). An *Aspergillus niger* β-glucosidase enzyme (Novozym 50010; Novozymes) was was added to provide 40.0 CBU/g glucan (CBU=cellobiase unit expressed as moles of cellubiose converted to glucose per minute). A *S. cerevisiae* strain Y-1528 inoculum prepared as described in Example 1, was added to the reaction mixture at a concentration of 5 g/L. The flasks were prepared in triplicate. Ten Zirconium mixing balls were added to each flask after which, the flasks were incubated at 36° C. under micro-aerobic conditions with agitation at 150 rpm. The flasks were sampled at 18 h, 25 h and 40 h. Ethanol production and monosaccharide concentrations in the sampled reaction mixtures were determined by GC and HPLC respectively. The data in FIG. 2 show that the SSF reaction process in terms of maximum ethanol production in this reaction mixture, was substantially completed within 25 hrs.

EXAMPLE 3

Figure 3:
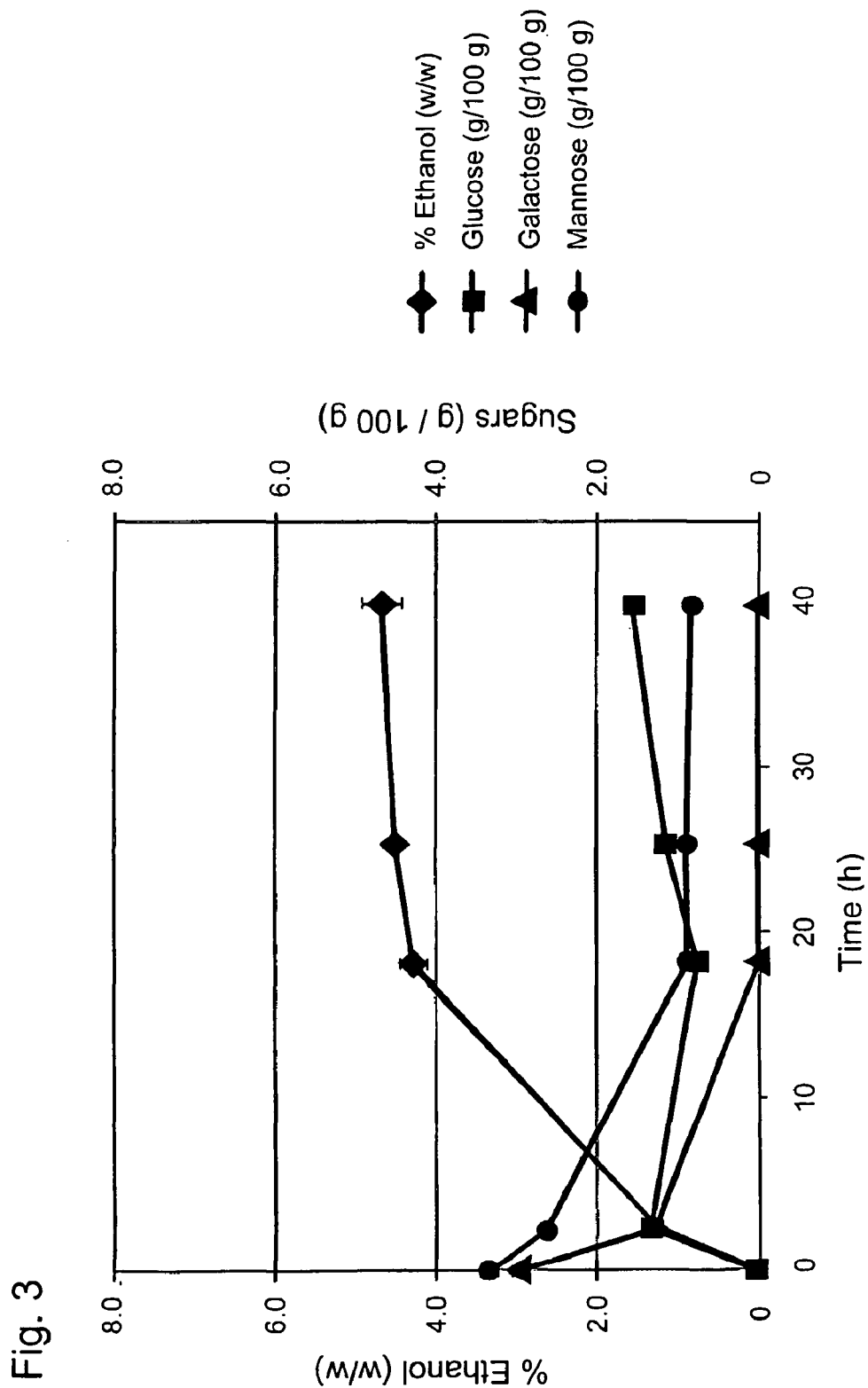
FIG. 3 is a chart showing the rate of ethanol production by *S. cerevisiae* strain Y-1528 when cultured in a simultaneous saccharification and fermentation system with a hardwood solid fraction obtained from aspen by Lignol lab-scale pretreatment technology supplemented with galactose and mannose, as the fermentation substrate. The data points are averages of triplicate samples. The bars extending above and below the data points represent±SD at 95% confidence. Data points without SD bars encompass the SD range for those data point.

The effects of supplementing the Asp4 "wet" pulp with galactose and mannose on ethanol production by S. cerevisiae strain Y-1528 in the SSF system described in Example 2, were assessed by adding galactose and mannose stock solutions to the citrate buffer component of the reaction mixture to provide final concentrations of 2.5 g/L of galactose and 2.5 g/L of mannose. The other reaction components i.e., Asp4 pulp, nutrients, enzymes and yeast inocula were the same as described in Example 2. The flasks were prepared in triplicate. Ten Zirconium mixing balls were added to each flask after which, the flasks were incubated at 36° C. under micro-aerobic conditions with agitation at 150 rpm. The flasks were sampled at 4 h, 18 h, 25 h and 40 h. Ethanol production and monosaccharide concentrations in the sampled reaction mixtures were determined by GC and HPLC respectively. The data in FIG. 3 show that enzymatic activity was maintained during the 40-h SSF reaction process as evidenced by the decrease in glucose levels during the first 25 h followed by increases at the subsequent sampling periods while mannose and galactose levels decreased during the first 25 h after which they were constant. Significant ethanol production occurred during the first 25 h and although the rate of ethanol production declined for the duration of the study, increasing concentrations of ethanol were recorded at each sampling period.

EXAMPLE 4

Figure 4:
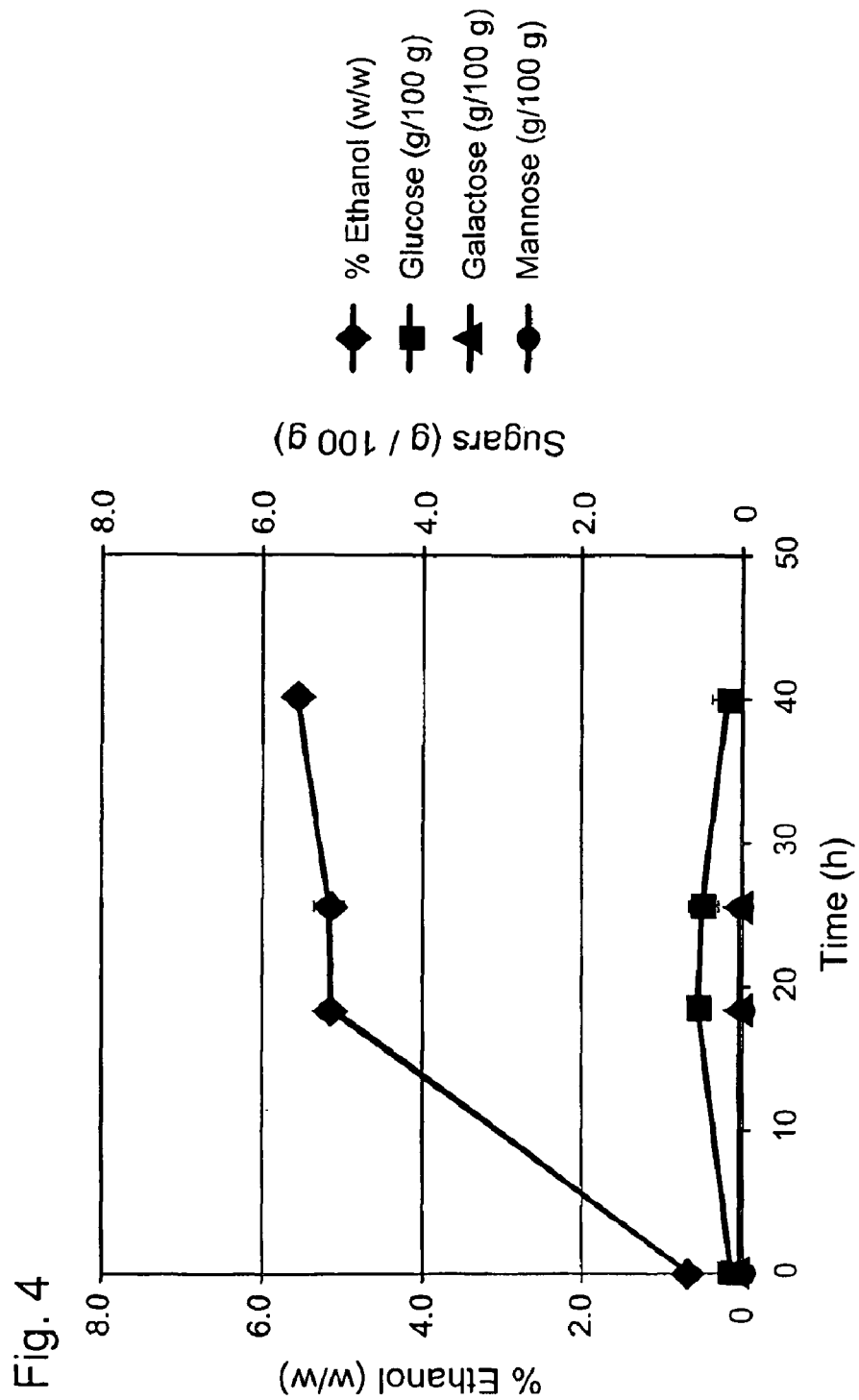
FIG. 4 is a chart showing the rate of ethanol production by *S. cerevisiae* strain Y-1528 when cultured for 16 h in a galactose/mannose substrate prior to its incorporation into a simultaneous saccharification and fermentation system with a hardwood solid fraction obtained from aspen by Lignol lab-scale pretreatment technology supplemented as the fermentation substrate. The data points are averages of triplicate samples. The bars extending above and below the data points represent±SD at 95% confidence. Data points without SD bars encompass the SD range for those data point.

The effects of conditioning the S. cerevisiae strain Y-1528 by culturing the yeast in a saccharide medium to initiate its fermentive activities for 16 hr, and then transferring the actively fermenting yeast into the SSF system described in Example were assessed in this study. A conditioning culture solution comprising 0.1 M citrate buffer adjusted to pH 5.5 was supplemented with 2.5 g/L of galactose and 2.5 g/L of mannose. The conditioning culture solution was inoculated with 5 g/L inoculum prepared as outlined in Example 1. The conditioning culture solution was incubated for 16 h at 30° C. under micro-aerobic conditions with agitation at 250 rpm. Then 68.24 mL of the conditioned culture solution were withdrawn and supplemented with 8.51 mL of fresh 0.1 M citrate buffer. The buffer-supplemented conditioned culture solution was then used to prepare the galactose- and mannose-supplemented reaction mixture described in Example 3. The flasks were prepared in triplicate. Ten Zirconium mixing balls were added to each flask after which, the flasks were incubated at 36° C. under micro-aerobic conditions with agitation at 150 rpm. The flasks were sampled at 18 h, 25 h and 40 h. Ethanol production and monosaccharide concentrations in the sampled reaction mixtures were determined by GC and HPLC respectively. The data in FIG. 4 show that addition of the conditioned yeast into the galactose- and mannose-supplemented reaction mixture enabled fermentation to proceed through to the end of the 40-h SSF period.

EXAMPLE 5

Figure 5:
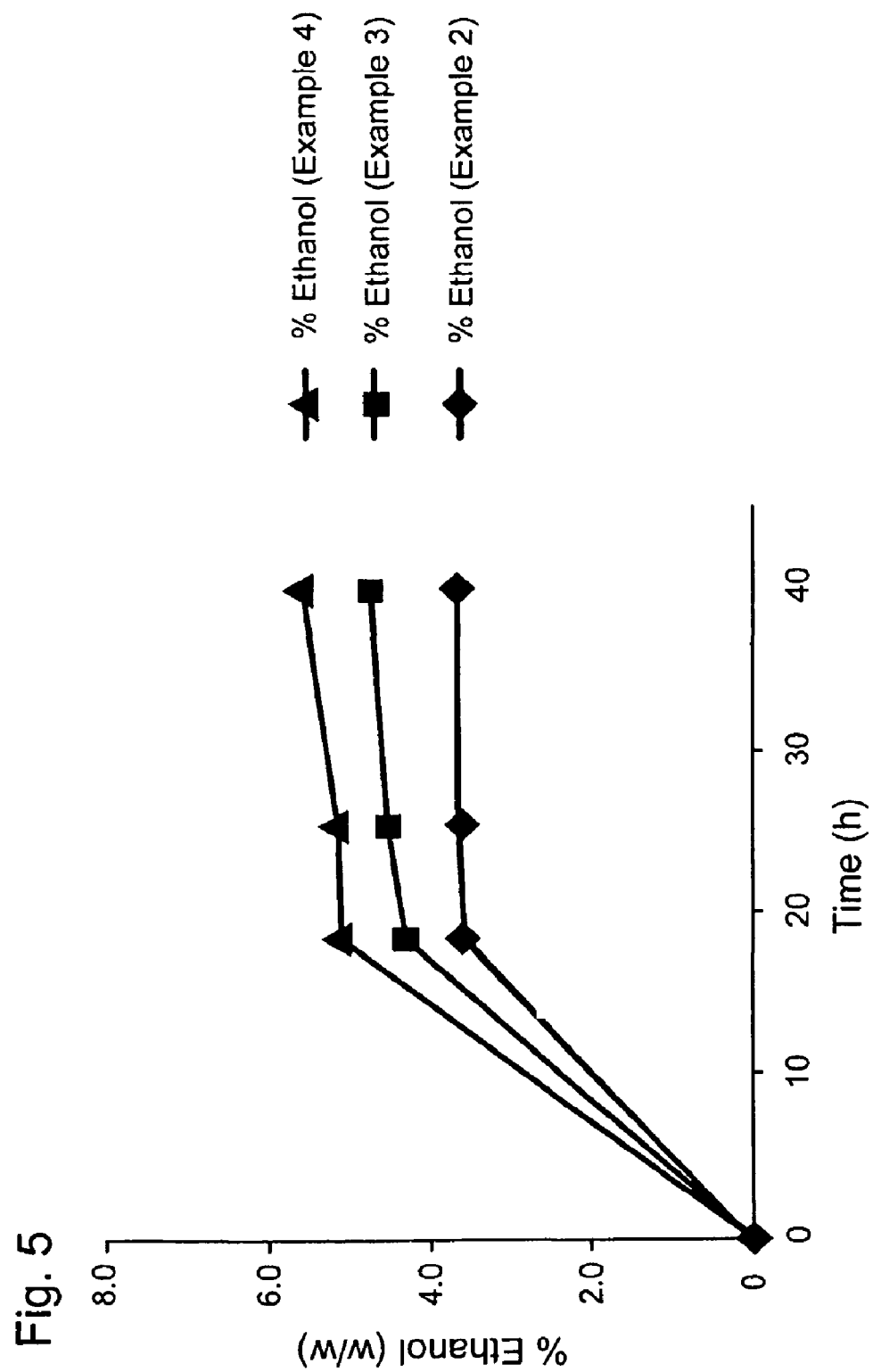
FIG. 5 is a chart comparing the rates of ethanol production by *S. cerevisiae* strain Y-1528 in the three systems shown in FIGS. 2-4. The data points are averages of triplicate samples. The bars extending above and below the data points represent±SD at 95% confidence. Data points without SD bars encompass the SD range for those data point.

The ethanol production performance of S. cerevisiae strain Y-1528 in the three SSF conditions described in Examples 2-4, is shown in FIG. 5. When this strain was used in a SSF process at 36° C. using a cellulosic pulp as the fermentation substrate, its ethanol yield was 3.65% ethanol (w/w) which was calculated to be 84% at 18 h and at 40 h was 86%, both compared to the theoretical yield (FIG. 5; Example 2). Addition of 2.5 g/L galactose and 2.5 g/L mannose to the fermentation substrate increased ethanol production to 4.68% (w/w) which was determined to be 78% of the potential theoretical yield at 18 h and 85% of the theoretical yield at 40 h (FIG. 5; Example 3). Pre-conditioning the yeast strain by culturing in a medium containing two monosaccharides, and then adding it to a galactose- and mannose-supplement fermentation medium further increase ethanol production in the SSF system to 5.56% (w/w) in the same time period; this amount was calculate to be 93% of the theoretical yield at 18 h and 100% of the theoretical yield at 40 h (FIG. 5; Example 4).

While this invention has been described with respect to the exemplary embodiments, those skilled in these arts will understand how to modify and adapt the processes, systems, and methods disclosed herein for concurrent saccharification and fermentation of solids and liquids fractions separated from extracted lignocellulosic feedstocks, by reducing the viscosity of the solids fractions by intermixing with a suitably selected liquid stream, then commingling therein effective amounts of a suitable microbial inoculum, and suitable enzymes. In view of numerous changes and variations that will be apparent to persons skilled in these arts, the scope of the present invention is to be considered limited solely by the appended claims.

What is claimed is:

1. A process for simultaneous saccharification and fermentation of a cellulosic solids fraction extracted from a lignocellulosic feedstock, the process comprising the steps of:
   separating an extracted lignocellulosic feed stock into a cellulosic solids fraction and a liquids fraction;
   processing said liquids fraction to remove extracted lignins therefrom thereby producing a de-lignified liquids fraction;
   reducing the viscosity of the separated cellulosic solids fraction by intermixing said cellulosic solids fraction with a portion of said de-lignified liquids fraction;
   intermixing the reduced-viscosity cellulosic solids fraction with (a) an effective amount of a fermentative microbial culture, and (b) an effective amount of a cellulosic biomass-degrading enzyme;
   commingling said microbial culture, said biomass-degrading enzyme and said reduced-viscosity cellulosic solids fraction to provide a reaction mixture comprising ethanol; and
   separating ethanol from said reaction mixture.

2. A process according to claim 1, wherein said de-lignified liquids fraction is intermixed with a liquid carbohydrate stream.

3. A process according to claim 1, wherein said liquid carbohydrate stream contains one of glucose, galactose, mannose, xylose or mixtures thereof.

4. A process according to claim 1, wherein said de-lignified liquids fraction is additionally processed to remove at least one of acetic acid, furfural and 5-hydoxymethyl-2-furfural prior to intermixing with the cellulosic solids fraction.

5. A process according to claim 1, wherein said lignocellulosic feedstock is selected from the group consisting angiosperm biomass, gymnosperm biomass, field crop biomass, vegetative and/or fruit pulps, wood and wood processing scraps and waste materials, recyclable paper and cardboard goods.

6. A process according to claim 1, wherein the fermentative microbial culture is a strain selected from the group consisting of yeast species, fungal species, and bacterial species.

7. A process according to claim 6, wherein the fermentative microbial culture is a strain selected from the group consisting of naturally occurring strains and genetically modified strains.

8. A process according to claim 7, wherein the fermentative microbial culture is a strain selected from the group consisting of *Saccharomyces* spp.

9. A process according to claim 8, wherein the fermentative microbial culture is *Saccharomyces cerevisiae* strain Y-1528.

10. A process according to claim 7, wherein the fermentative microbial culture is a fungal strain selected from the group consisting of *Trichoderma* spp. and *Aspergillus* spp.

11. A process according to claim 7, wherein the fermentative microbial culture is a bacterial strain selected from the group consisting of *Zymomonas* spp., *Corynebacterim* spp., *Clostridium* spp. and *Escherichia coli*.

12. A process according to claim 1, wherein the cellulosic biomass-degrading enzyme is selected from the group consisting of cellulases, β-glucosidases, hemicellulases, β-xylosidases, and mixtures thereof.

13. A process according to claim 1, wherein the process is a batch process.

14. A process according to claim 1, wherein the process is a continuous process.

15. A process according to claim 1, wherein the process is a semi-continuous process.

16. A process for simultaneous saccharification and fermentation of a cellulosic solids fraction extracted and separated from a lignocellulosic feedstock, the process comprising the steps of:
    reducing the viscosity of the separated cellulosic solids fraction by intermixing said cellulosic solids fraction with a liquid stream comprising at least one monosaccharide carbohydrate;
    intermixing the reduced-viscosity cellulosic solids fraction with (a) an effective amount of a fermentative microbial culture, and (b) an effective amount of a cellulosic biomass-degrading enzyme;
    commingling said microbial culture, said biomass-degrading enzyme and said reduced-viscosity cellulosic solids fraction to provide a reaction mixture comprising ethanol; and
    separating ethanol from said reaction mixture.

17. A process according to claim 16, wherein the liquid stream comprises a monosaccharide selected from the group consisting of glucose, mannose, galactose, xylose, and mixtures thereof.

18. A process according to claim 16, wherein said lignocellulosic feedstock is selected from the group consisting angiosperm biomass, gymnosperm biomass, field crop biomass, vegetative and/or fruit pulps, wood and wood processing scraps and waste materials, recyclable paper and cardboard goods.

19. A process according to claim 16, wherein the fermentative microbial culture is a strain selected from the group consisting of yeast species, fungal species, and bacterial species.

20. A process according to claim 19, wherein the fermentative microbial culture is a strain selected from the group consisting of naturally occurring strains and genetically modified strains.

21. A process according to claim 20, wherein the fermentative microbial culture is a strain selected from the group consisting of *Saccharomyces* spp.

22. A process according to claim 21, wherein the fermentative microbial culture is *Saccharomyces cerevisiae* strain Y1528.

23. A process according to claim 20, wherein the fermentative microbial culture is a fungal strain selected from the group consisting of *Trichoderma* spp. and *Aspergillus* spp.

24. A process according to claim 20, wherein the fermentative microbial culture is a bacterial strain selected from the group consisting of *Zymomonas* spp., *Corynebacterim* spp., *Clostridium* spp. and *Escherichia coli*.

25. A process according to claim 16, wherein the cellulosic biomass-degrading enzyme is selected from the group consisting of cellulases, β-glucosidases, hemicellulases, β-xylosidases, and mixtures thereof.

26. A process according to claim 16, wherein the process is a batch process.

27. A process according to claim 16, wherein the process is a continuous process.

28. A process according to claim 16, wherein the process is a semi-continuous process.

* * * * *